US012324890B2

(12) United States Patent
Smith et al.

(10) Patent No.: US 12,324,890 B2
(45) Date of Patent: Jun. 10, 2025

(54) MEDICAL DELIVERY DEVICE AND METHOD OF USE

(71) Applicant: Boston Scientific Scimed, Inc., Maple Grove, MN (US)

(72) Inventors: Amanda Smith, Boston, MA (US); Jennifer Mague, Marlborough, MA (US); Andrew Pic, Northboro, MA (US); Joseph King, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 830 days.

(21) Appl. No.: 17/103,681

(22) Filed: Nov. 24, 2020

(65) Prior Publication Data

US 2021/0162189 A1 Jun. 3, 2021

Related U.S. Application Data

(60) Provisional application No. 62/942,919, filed on Dec. 3, 2019.

(51) Int. Cl.
*A61M 31/00* (2006.01)
*A61B 1/018* (2006.01)
*A61B 17/00* (2006.01)
*A61B 17/29* (2006.01)

(52) U.S. Cl.
CPC ............ *A61M 31/002* (2013.01); *A61B 1/018* (2013.01); *A61B 17/29* (2013.01); *A61B 2017/00336* (2013.01); *A61B 2017/0034* (2013.01)

(58) Field of Classification Search
CPC ............ A61M 31/002; A61M 25/0662; A61M 25/0082; A61B 1/018; A61B 17/29; A61B 2017/00336; A61B 2017/0034; A61B 17/00491; A61B 2017/003; A61B 2217/005; A61B 2217/007
See application file for complete search history.

(56) References Cited

U.S. PATENT DOCUMENTS

| | | | | |
|---|---|---|---|---|
| 4,900,303 A * | 2/1990 | Lemelson | ......... | A61M 37/0069 604/11 |
| 5,011,488 A * | 4/1991 | Ginsburg | ......... | A61B 17/22032 604/908 |
| 5,800,457 A * | 9/1998 | Gelbfish | ............... | A61F 2/0105 606/200 |
| 6,899,672 B2 * | 5/2005 | Chin | .................... | A61B 1/0684 600/143 |
| 9,173,694 B2 * | 11/2015 | Kleiner | .............. | A61B 17/8819 |
| 11,583,170 B2 * | 2/2023 | Harris | ................ | A61B 1/00183 |

(Continued)

FOREIGN PATENT DOCUMENTS

| CN | 101146484 A | 3/2008 |
|---|---|---|
| CN | 103391797 A | 11/2013 |

(Continued)

*Primary Examiner* — Anh Tuan T Nguyen
*Assistant Examiner* — Shankar Raj Ghimire
(74) *Attorney, Agent, or Firm* — Bookoff McAndrews, PLLC (57) ABSTRACT

A medical system includes a handle, a sheath extending from the handle, and an end effector connected to a distal end of the sheath, where the end effector directs a mass of material towards a target site of a body and cause release of the material onto the target site.

3 Claims, 7 Drawing Sheets

(56) References Cited

U.S. PATENT DOCUMENTS

| | | | |
|---|---|---|---|
| 2001/0047135 A1* | 11/2001 | Daniels | A61B 1/00165 600/478 |
| 2002/0019635 A1* | 2/2002 | Wenstrom, Jr. | A61F 2/0811 606/88 |
| 2003/0094173 A1* | 5/2003 | Burr | A61M 15/0028 222/394 |
| 2003/0150454 A1* | 8/2003 | Burr | A61M 15/0028 128/203.12 |
| 2003/0236573 A1 | 12/2003 | Evans et al. | |
| 2005/0165272 A1* | 7/2005 | Okada | A61B 17/0469 600/113 |
| 2006/0036182 A1* | 2/2006 | Daniels | A61B 5/0084 600/478 |
| 2006/0058838 A1* | 3/2006 | Bose | A61B 17/221 606/200 |
| 2007/0191768 A1 | 8/2007 | Kolb | |
| 2008/0021444 A1* | 1/2008 | Scoption | A61B 1/018 606/37 |
| 2008/0312664 A1* | 12/2008 | Bardsley | A61B 17/1285 606/151 |
| 2009/0287183 A1* | 11/2009 | Bishop | A61M 25/0662 604/509 |
| 2009/0306470 A1* | 12/2009 | Karasawa | A61B 1/04 600/103 |
| 2010/0256446 A1* | 10/2010 | Raju | A61B 1/00091 600/114 |
| 2010/0298642 A1* | 11/2010 | Trusty | A61B 1/00135 600/114 |
| 2011/0152763 A1* | 6/2011 | Bishop | A61M 29/00 604/101.01 |
| 2011/0251682 A1* | 10/2011 | Murray, III | A61F 2/2436 623/2.11 |
| 2012/0035588 A1* | 2/2012 | Schoenle | A61M 25/1011 604/101.02 |
| 2014/0066967 A1* | 3/2014 | Levy | A61M 31/002 606/191 |
| 2014/0135810 A1 | 5/2014 | Divino et al. | |
| 2014/0243953 A1* | 8/2014 | Stante | A61F 2/966 623/2.11 |
| 2014/0302133 A1* | 10/2014 | Van Rooyen | A61K 9/4808 424/453 |
| 2015/0173769 A1* | 6/2015 | Durgin | A61B 34/71 606/142 |
| 2017/0112624 A1* | 4/2017 | Patel | A61F 2/2436 |
| 2017/0319222 A1* | 11/2017 | Chu | A61B 17/00234 |
| 2018/0035997 A1* | 2/2018 | Smith | A61B 17/1285 |
| 2018/0353198 A1* | 12/2018 | Kline | A61B 17/3421 |
| 2018/0361065 A1* | 12/2018 | Trezza | A61M 5/19 |
| 2020/0253639 A1* | 8/2020 | Kim | A61B 17/29 |
| 2020/0323422 A1* | 10/2020 | Duan | A61B 1/041 |
| 2021/0236100 A1* | 8/2021 | Sharma | A61B 1/018 |
| 2021/0268241 A1* | 9/2021 | Lydecker | A61M 1/84 |
| 2022/0022736 A1* | 1/2022 | Duan | A61B 1/273 |
| 2022/0323637 A1* | 10/2022 | Greenawalt | C07K 14/76 |

FOREIGN PATENT DOCUMENTS

| | | |
|---|---|---|
| CN | 109152570 A | 1/2019 |
| EP | 1 974 685 A1 | 10/2008 |
| WO | 00/03691 A1 | 1/2000 |
| WO | 01/02042 A1 | 1/2001 |
| WO | 01/15608 A1 | 3/2001 |
| WO | 2006/081238 A2 | 8/2006 |

* cited by examiner

MEDICAL DELIVERY DEVICE AND METHOD OF USE

CROSS-REFERENCE TO RELATED APPLICATIONS

This application claims the benefit of priority from U.S. Provisional Application No. 62/942,919, filed on Dec. 3, 2019, which is incorporated by reference herein in its entirety.

TECHNICAL FIELD

The present disclosure relates generally to endoscopic medical devices and related methods of use. More particularly, in some embodiments, the disclosure relates to endoscopic medical tools and methods related to accessing target sites and dispensing materials to the target sites.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may not achieve a desired rate of agent delivery or a desired dosage of agent, may result in inconsistent dosing of agent, or may not result in the agent reaching the treatment site deep within the GI tract. The current disclosure may solve one or more of these issues or other issues in the art.

SUMMARY OF THE DISCLOSURE

According to an embodiment, a medical system includes a handle, a sheath extending from the handle, and an end effector connected to a distal end of the sheath, wherein the end effector is configured to direct a mass of material towards a target site of a body and cause release of the material onto the target site.

The medical system may include a catheter including a catheter lumen, wherein the sheath may be configured to extend through the catheter lumen, and wherein the catheter may further include a fluid lumen, fluidly decoupled from the catheter lumen, wherein the fluid lumen may be configured to be attached to a fluid source and may dispense a fluid from a fluid opening at a distal end of the catheter.

The medical system may further include a capsule containing the mass of material, wherein the end effector may be configured to advance the capsule along the catheter lumen and to the target site via a lumen opening at a distal end of the catheter.

The end effector may include a pair of jaws, and wherein the capsule may include a tether configured to be grasped by the pair of jaws.

The end effector may be configured to pull on the tether to open the capsule.

An outer covering of the capsule may include a material configured to adhere to the target site when exposed to fluid.

An outer covering of the capsule may include a material that dissolves when contacted with fluid.

The end effector may be configured to move from a collapsed configuration to an expanded configuration, wherein the end effector may have an umbrella-like shape in the expanded configuration such that a diameter of a distal end of the end effector may be greater than a diameter of a proximal end of the end effector.

The catheter may include the capsule within the catheter lumen.

The end effector may include a shape memory material, wherein a temperature of the end effector may be configured to be increased by a heat from the body, and wherein the end effector may expand from the collapsed configuration to the expanded configuration when the end effector is above a temperature threshold.

The catheter may include a capsule containing the mass of material, wherein a diameter of a distal opening of the catheter lumen may be less than a diameter of the capsule.

The distal end of the catheter lumen may include a protrusion extending from a wall of the catheter lumen toward a central longitudinal axis of the catheter configured to rupture the capsule.

A diameter of the end effector may be less than the diameter of the distal opening of the catheter lumen, and wherein the end effector may be configured to extend out of the catheter lumen and distal of a distalmost end of the catheter.

The end effector may have a disc-shaped distal surface for applying pressure to the material at the target site.

The material may be a hemostatic agent or a therapeutic agent.

According to another embodiment, a medical system includes an actuation handle, a sheath extending from a distal end of the handle, a catheter including a catheter lumen, wherein the sheath is configured to extend through the catheter lumen, a capsule containing a material wherein the capsule includes a tether, and an end effector connected to a distal end of the sheath and configured to grasp the tether, wherein the end effector is configured to advance the capsule along the catheter lumen and to a target site via a catheter lumen opening at a distal end of the catheter, wherein an outer portion of the capsule includes a material configured to adhere to the target site when exposed to a fluid, and wherein the end effector is configured to cause release of the material from the capsule and onto the target site by applying a force on the tether once the capsule is adhered to the target site.

A distal end of the catheter or the sheath may be configured to bend when the distal end of the sheath is distal of a distalmost end of the catheter.

According to yet another embodiment, a method of performing a medical procedure includes positioning a catheter adjacent a target site within a body, advancing a sheath distally along a lumen of the catheter, pushing a capsule containing a material along the lumen using an end effector on a distal end of the sheath, expelling the capsule from a distal end of the lumen towards the target site, and releasing the material from the capsule.

The method may further include attaching the capsule to the target site, and maneuvering the end effector away from the target site after the capsule is attached to the target site, causing the capsule to rupture.

The method may further include actuating the end effector to release the capsule in the body after the capsule is ruptured, and moving the sheath proximally to cause the end effector to reenter the lumen.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

The present disclosure is now described with reference to an exemplary medical system that may be used to dispense materials endoscopically. However, it should be noted that reference to this particular procedure is provided only for convenience and not intended to limit the disclosure. A person of ordinary skill in the art would recognize that the concepts underlying the disclosed device and application method may be utilized in any suitable procedure, medical or otherwise. The present disclosure may be understood with reference to the following description and the appended drawings, wherein like elements are referred to with the same reference numerals.

For ease of description, the term "distal" refers to a portion farthest away from a user when introducing the system into a patient. By contrast, the term "proximal" refers to a portion closest to the user when introducing the system into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." In this disclosure, relative terms, such as, for example, "about," "substantially," "generally," and "approximately" are used to indicate a possible variation of ±10% in a stated value or characteristic.

Figure 1:
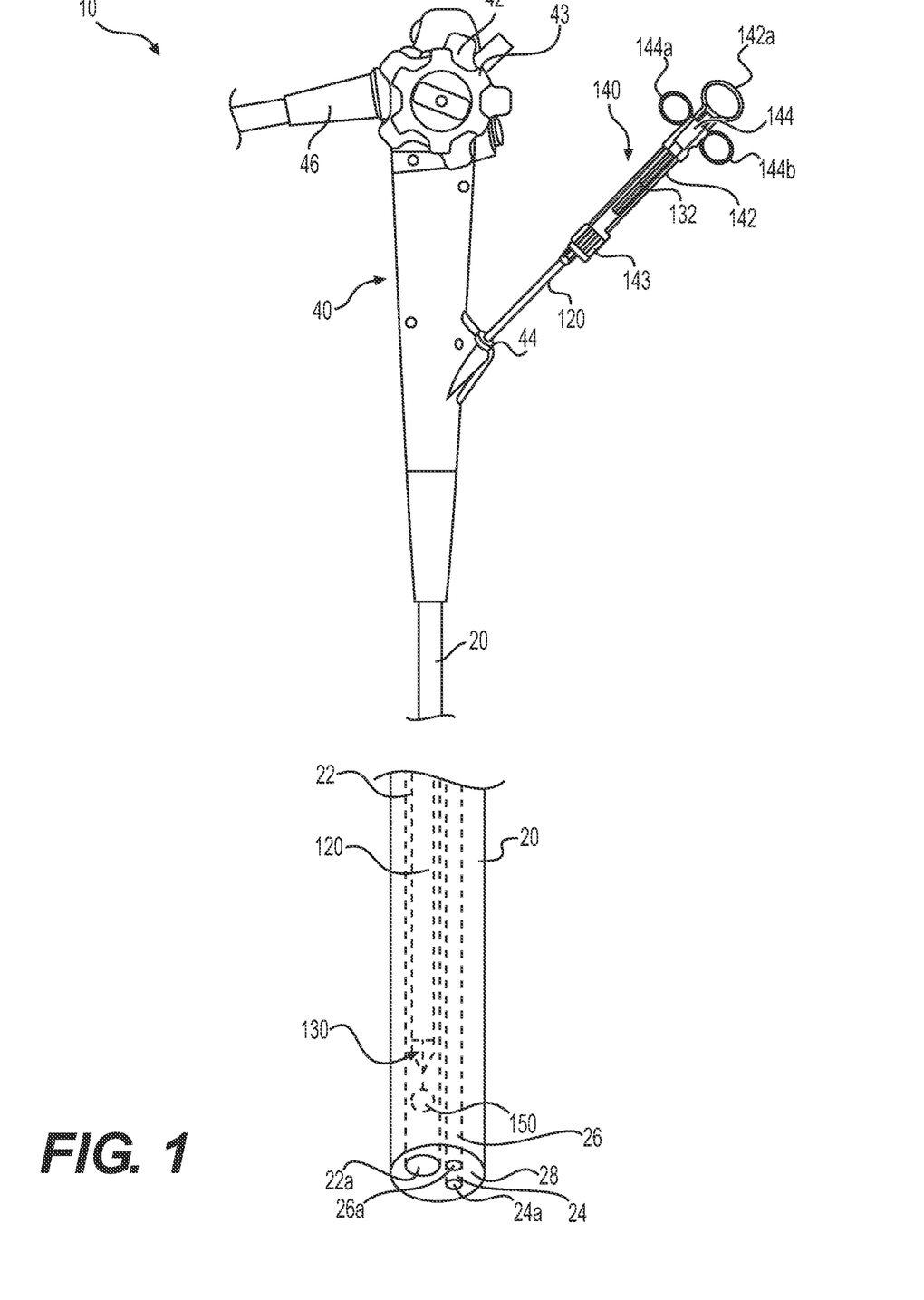
FIG. 1 is a perspective view of a medical system according to an embodiment.

Referring to FIG. 1, a medical system 10 according to an embodiment is shown. Medical system 10 includes a flexible shaft 20 (e.g., a catheter) and a handle 40 connected at a proximal end of flexible shaft 20. Handle 40, or some other device for actuating or controlling medical system 10 and any tool or devices associated with medical system 10, includes first and second actuating devices 42, 43, which control articulation of flexible shaft 20, and/or an articulation joint at a distal end of flexible shaft 20, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of endoscope 10 and connect to flexible shaft 20 to control movement thereof. Alternatively, or additionally, a user may operate actuating elements independently of handle 40. Distal ends of actuating elements extend through flexible shaft 20 and terminate at an actuating joint and/or a distal tip of flexible shaft 20. For example, one or more actuating elements may be connected to an articulation joint, and actuation of actuating elements may control the actuating joint or the distal end of flexible shaft 20 to move in multiple directions.

In addition, one or more electrical cables (not shown) may extend from the proximal end of endoscope 10 to the distal end of flexible shaft 20 and may provide electrical controls to imaging, lighting, and/or other electrical devices at the distal end of flexible shaft 20, and may carry imaging signals from the distal end of flexible shaft 20 proximally to be processed and/or displayed on a display. Handle 40 may also include ports 44, 46 for introducing and/or removing tools, fluids, or other materials from the patient. Port 44 may be used to introduce tools. Port 46 may be connected to an umbilicus for introducing fluid, suction, and/or wiring for electronic components. For example, as shown in FIG. 1, port 44 is connected to a lumen 22, which extends from the proximal end to the distal end of flexible shaft 20. Port 44 may receive a medical device, such as flexible sheath 120 (e.g., a catheter) of a medical device.

As shown in FIG. 1, sheath 120 is attached to a distal end of a handle 140. Handle 140 includes a body 142 defining a hole 142a at a proximal end thereof. Sheath 120 is attached at a distal end of body 142, opposite hole 142a. Hole 142a may accommodate a thumb (or a finger) of a user. Handle 140 may be integrally formed with or otherwise fixedly attached to sheath 120.

As further illustrated in FIG. 1, a slot extends through body 142 in a direction parallel to a longitudinal axis of sheath 120 and body 142. A portion of a spool 144 (e.g., a slidable member) is disposed in the slot and may move within the slot and along body 142 in a direction parallel to the longitudinal axis. As further shown in FIG. 1, spool 144 includes two circular grasping elements 144a, 144b, each having a hole therethrough, extending from spool 144 transverse to the longitudinal axis. Grasping elements 144a, 144b are illustrated as being separated 180 degrees from each other about the longitudinal axis, but the positioning of grasping elements 144a, 144b is not limited thereto. Grasping elements 144a, 144b are grasped by a user to move spool 144 along body 142. For example, a user may place a thumb in hole 142a, an index finger in grasping element 144a, and a middle finger in grasping element 144b, allowing the user to move spool 144 along the longitudinal axis. Wire 132 is connected to and extends distally from the distal end of spool 144. Wire 132 extends through a hole (not shown) at the distal end of body 142 and through a lumen (not shown) of sheath 120. Movement of wire 132 along the longitudinal axis, relative to sheath 120, actuates end effector 130, as will be explained herein. Alternatively, wire 132 may be rotatable about a rotation mechanism 143, such as a screw mechanism or any other mechanism known in the art.

Figure 2:
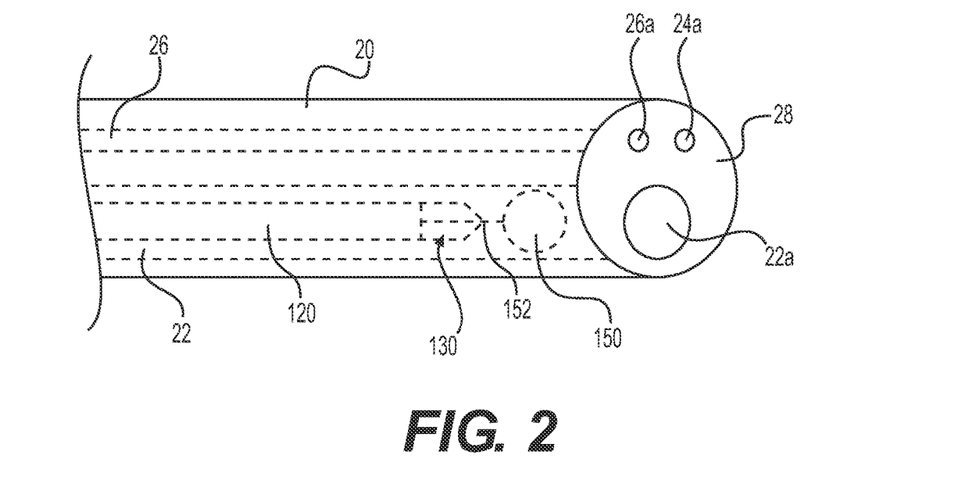
FIG. 2 is a perspective view of a medical tool of the medical system of FIG. 1, according to an embodiment.
Figure 3:
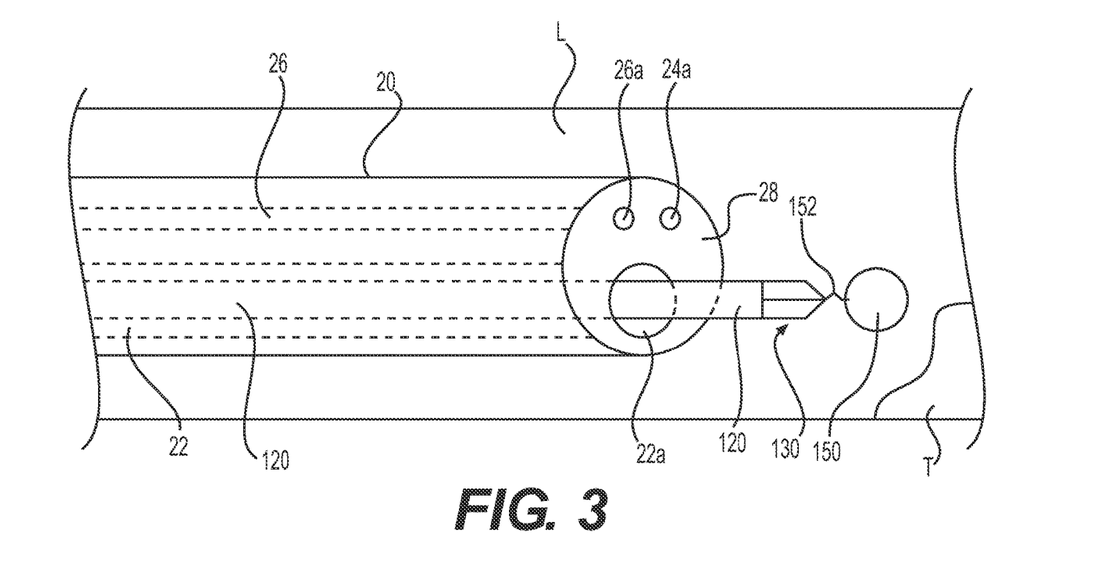
FIGS. 3-5 are perspective views of the medical tool of FIG. 2.
Figure 4:
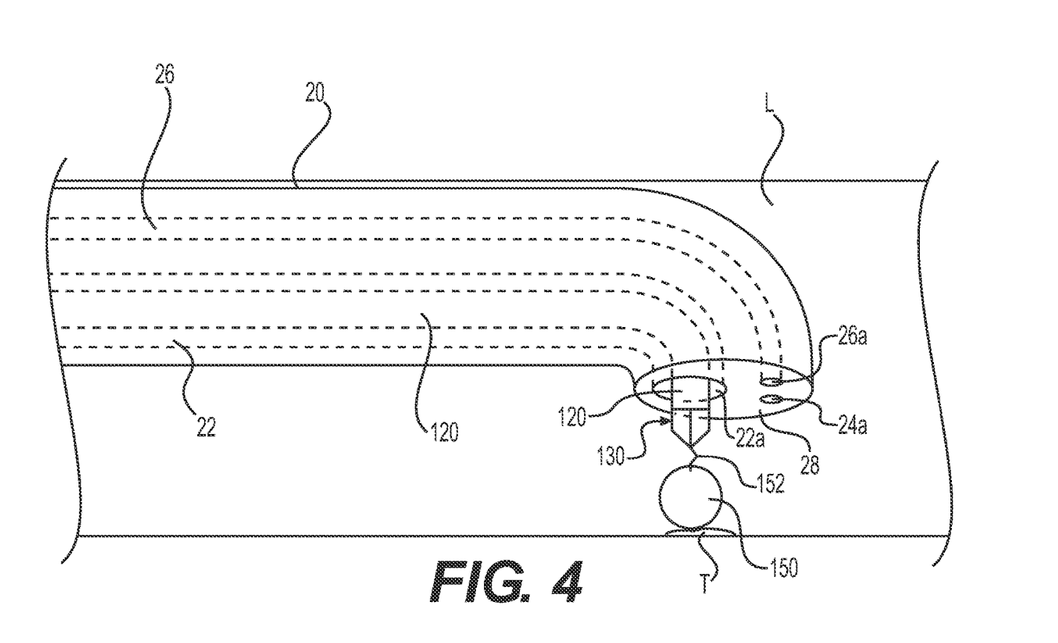

Referring to FIGS. 2-4, catheter 20 includes a plurality of lumens, e.g., a first lumen 22, a second lumen 24 (for ease of description, second lumen 24 is shown only in FIG. 1), and a third lumen 26. According to an example, first lumen 22 is configured to receive sheath 120 of the medical device, as will be described in greater detail herein. First lumen 22 extends from handle 40 and terminates at a first opening 22a at a distal end face 28 of catheter 20. Second and third lumens 24, 26 may receive additional tools, and/or may be used for suction/vacuum, dispensing fluid, imaging, illumination, or the like. For example, distal openings 24a, 26a of second and third lumens 24, 26 may be open at distal end face 28 of catheter 20. According to an example, fluid may be expelled through one or both of openings 24a, 26a after traveling along respective second and third lumens 24, 26 from handle 40. Alternatively, debris may be suctioned/vacuumed through one or both of openings 24a, 26a, and/or an electrical fiber may be disposed in on or both of second and third lumens 24, 26 and attached to a visualization component, such as a camera, or an illumination member, such as a light emitting diode (LED), disposed at openings 24a, 26a. It will be understood that these components may be fixed in openings 24a, 26a, or the components may be extended from distal end face 28 to provide additional illumination of and/or visualization of a target site T.

With continued reference to FIG. 2, sheath 120 extends within first lumen 22 of catheter 20. Sheath 120 is flexible and has an outer diameter less than an inner diameter of first lumen 22, thereby allowing sheath 120 to slide within and along first lumen 22. Sheath 120 includes an end effector 130 at a distalmost end. End effector 130 includes a pair of jaws which are actuatable between an open position and a closed position. End effector 130 is configured to grasp a tether 152 of a capsule 150, as shown in FIG. 2, to manipulate capsule 150 and to release contents from capsule 150, as will be described herein. It will be understood that end effector 130 is not limited to this arrangement, and may be any end effector suitable for performing a medical treatment at a target site. End effector 130 may be any suitable end effector used in a medical procedure, such as scissors, graspers, forceps, needle, etc., or any other therapeutic or diagnostic tool or device, for advancing capsule 150 to target site T and releasing a material 160 from capsule 150, as will be described herein. In embodiments, capsule 150 does not include a tether 152 and may be grasped about its perimeter. In some embodiments, capsule 150 may be attached to and/or delivered by one or more hemostatic clips, and material 160 may be released in any manner described herein.

FIG. 3 illustrates catheter 20 disposed in lumen L of a body and adjacent target site T. Sheath 120 is advanced along first lumen 22 using handle 140 to expose end effector 130 and capsule 150 from distal end face 28 of catheter 20, by inserting catheter 20 through port 44. For example, a user may maneuver handle 140 to move sheath 120 distally with respect to catheter 20. This movement causes end effector 130 to push against a proximal side of capsule 150, exposing both capsule 150 and end effector 130 from first opening 22a. Handle 140 may be further maneuvered to move capsule 150 adjacent target site T. As described herein, openings 24a, 26a may include lighting and/or visualization elements, which may assist in the placement of capsule 140.

As shown in FIG. 3, target site T protrudes into lumen L. According to an example, sheath 120 may advance capsule 150 to target site T without needing to further actuate or bend sheath 120. However, in some examples, target site T may be located on a side of lumen L, as shown in FIG. 4, which requires end effector 130 to be maneuvered toward target site T. As discussed above, catheter 20 may include actuating elements, e.g., cables, extending from handle 40, to the distal end of catheter 20. Pulling on those cables can bend the end of catheter 20, as shown in FIG. 4. Alternatively, or additionally, sheath 120 may be actuated to be bent or turned to access target site T. For example, sheath 120 may include an actuation section just proximal of end effector 130, which allows sheath 120 to bend and access target site T. The actuation section may include a shape memory material, e.g., Nitinol, and may be pre-bent to a certain angle such that, when the actuation section is exposed to lumen L, the shape memory material heats up and bends to the preset bend angle. Alternatively, the actuation section may be actuated using cables, wires, or the like, and the bend angle may be selected by the physician during a medical procedure. In this manner, the physician may advance capsule 150 to target site T.

As shown in FIG. 4, sheath 120 maneuvers capsule 150 to target site T and capsule 150 is adjacent or contacting target site T. In some embodiments, capsule 150 may include an adhesive on an outer surface of capsule 150 and/or a covering of capsule 150 may become adhesive due to exposure to a mucousy or a moist body lumen, or from a fluid expelled via openings 24a or 26a. According to an example, such a capsule 150 may adhere to target site T with sufficient force to withstand a pulling force on tether 152, as will be described herein.

Figure 5:
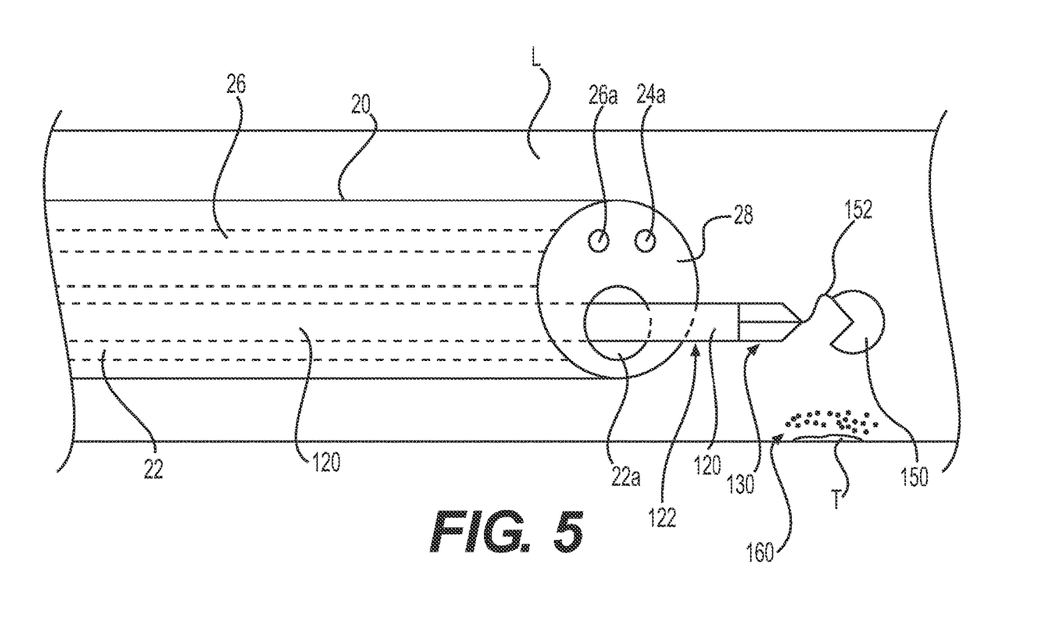

Once capsule 150 is properly positioned and attached to target site T, sheath 120 may be moved away from target site T to pull on tether 152 and release a material (e.g., a powder) 160, such as a medical or therapeutic agent, as shown in FIG. 5. For example, a physician may maneuver handle 140 such that sheath 120 is moved proximally, thereby moving end effector 130 away from target site T and exerting pressure on tether 152 and causing an outer wall of capsule 150 to break or tear open. Capsule 150 may include perforations or a similar feature that weakens at least a portion of a wall of the capsule, and exerting pressure on tether 152 may rupture the weakened portion of capsule 150. Capsule 150 may also include two sides of approximately equal size joined together, e.g., via a friction fit, an adhesive, a heat staking, or the like, and exerting pressure on tether 152 may cause the two sides to be pulled apart. Tether 152 may also be attached to a plug fit into a corresponding hole in capsule 150, such that exerting a force on tether 152 causes the plug to be removed from the hole. According to another example, tether 152 may be woven through overlapping flaps in capsule 150, and exerting pressure on tether 152 may compromise the seal. Once a seal or a wall of capsule 150 is broken, material 160 may exit capsule 150. Alternatively, or additionally, the physician may cause a distal actuation section of sheath 120 to otherwise bend and move end effector 130 away from target site T. As end effector 130 moves away from target site T, the adhesion forces acting on capsule 150 cause capsule 150 to remain adhered to target site T, causing tether 152 to break or produce a tear in capsule 150 and release powder 160. Powder 160 may be a hemostatic agent and may cause a bleed at target site T to coagulate. Alternatively, or additionally, powder 160 may include antibacterial and/or other beneficial medical properties to promote healing and/or other therapeutic benefits at target site T. After deploying powder 160, end effector 130 may be retracted into lumen 22 along with the remainder of the ruptured capsule 150. Alternatively, the physician may cause the jaws of end effector 130 to open to release tether 152 and allow capsule 150 to remain in the body to disintegrate and/or to be expelled via natural bodily excretion pathways. It will be understood that the powder-containing element is not limited to capsule 150. For example, capsule 150 may be any container suitable for containing powder 160 including, but not limited to, a spherical or other-shaped body having an outer protective layer surrounding powder 160. Alternatively, capsule 150 may not include an outer covering, and may be an agglomeration of powder 160, such as a mass of powder or other material, held together by an adhesive or other chemical bonds that break apart once exposed to a fluid. It will also be understood that capsule 150 may include compartments to include different types of material that, once exposed to each other, react to form a homogenous material with properties that cause the material to adhere to target site T and/or include therapeutic properties, such as a hemostatic agent.

In this manner, target sites that may be difficult to access, such as sites on a roof (top) of a gastrointestinal lumen, may have therapeutic powders applied thereto. It otherwise may be more difficult to apply powdered agents to target sites due to the gravitational forces applied to such powders. It will be understood that while catheter 20 is advanced to target site T and sheath 120 is advanced along first lumen 22 to target site T, catheter 20 is not necessary to deploy capsule 150. For example, sheath 120, including end effector 130 attached to capsule 150 via tether 152, may be advanced along a body lumen to target site T without the use of catheter 20.

A method of applying a therapeutic powder 160 will now be described.

Catheter 20 is inserted into a body through a natural orifice or an incision in a patient. Catheter 20 is advanced along a body lumen to target site T. Once catheter 20 is advanced to target site T, sheath 120 is inserted into port 44 and advanced along first lumen 22. It will be understood that sheath 120 may be inserted into port 44 prior to the beginning of the procedure, e.g., before inserting catheter 20 into the body, and sheath 120 may be advanced to target site T at a same time as catheter 20.

For example, capsule 150 may be inserted into port 44 prior to a distal end of sheath 120, or end effector 130 may grasp tether 152 prior to inserting capsule 150 and the distal end of sheath 120. Once both capsule 150 and sheath 120 are inserted into port 44, sheath 120 is advanced distally toward a distal end of catheter 20. As sheath 120 is advanced distally, end effector 130 pushes on a proximal end of capsule 150, causing capsule 150 to advance through lumen 22 of catheter 20. In an embodiment in which sheath 120 is inserted into a body without catheter 20, capsule 150 can also be moved to target site T in a similar manner. Alternatively, end effector 130 may pull capsule 150 along a body lumen L as sheath 120 is advanced distally toward target site T.

After positioning catheter 20 and sheath 120 adjacent target site T, handle 140 is manipulated to move sheath 120 along first lumen 22 in a distal direction with respect to catheter 20. Moving sheath 120 in the distal direction forces end effector 130 against the proximal side of capsule 150 and out first opening 22a in distal end face 28.

After capsule 150 is positioned outside first lumen 22, sheath 120 is maneuvered to urge capsule 150 against target site T. According to an example, urging capsule 150 against target site T may include bending a distal end of catheter 20 and/or bending an articulation section of sheath 120. In some examples, urging capsule 150 against target site T includes dispensing a fluid from openings 24a or 26a to moisten capsule 150 and activate an adhesive material on an outer surface of capsule 150.

Once capsule 150 is adhered to target site T, sheath 120 is moved away from target site T by moving sheath 120 proximally. Alternatively, end effector 130 may grasp capsule 150 between a pair of jaws. The jaws of end effector 130 may be actuated to increase pressure on capsule 150, thereby breaking the outer casing of capsule 150 and causing powder 160 to be dispersed at target site T. Sheath 120 is subsequently retracted into lumen 22 and catheter 20 may be removed from the body lumen. According to another example, prior to retracting sheath 120 into lumen 22, tether 152 may be released by pushing distally on spool 144 and opening the jaws of end effector 130. In an example where capsule 150 is dissolvable due to interaction with liquid, irrigation may be used to dissolve capsule 150 and release agent 160.

Figure 6A:
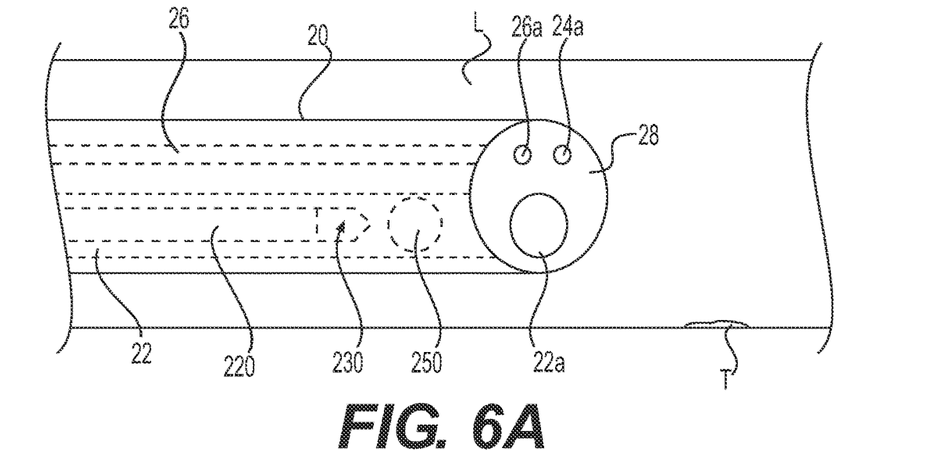
FIGS. 6A-6C are perspective views of a medical tool of the medical system of FIG. 1, according to another embodiment.
Figure 6B:
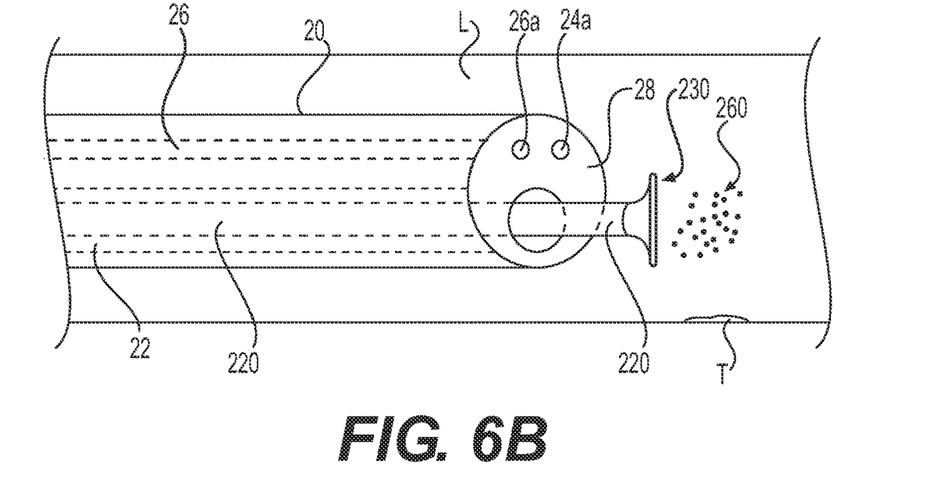
Figure 6C:
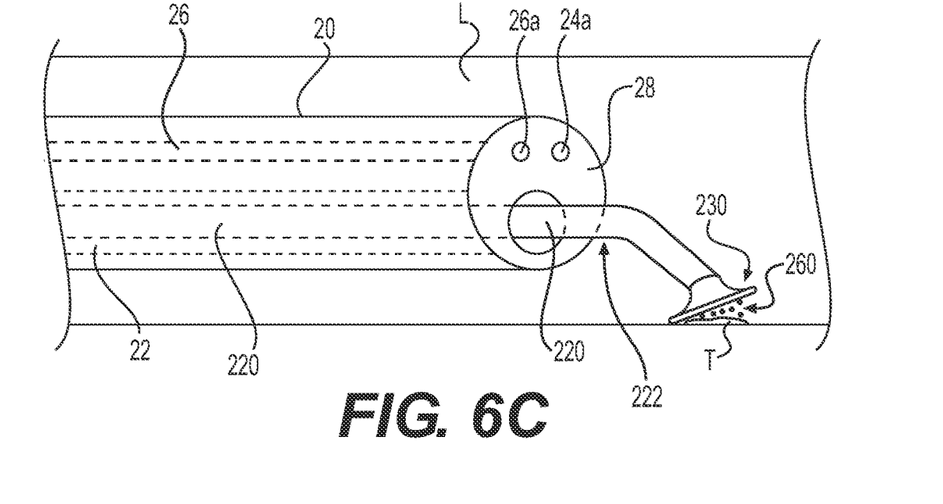
Figure 7A:
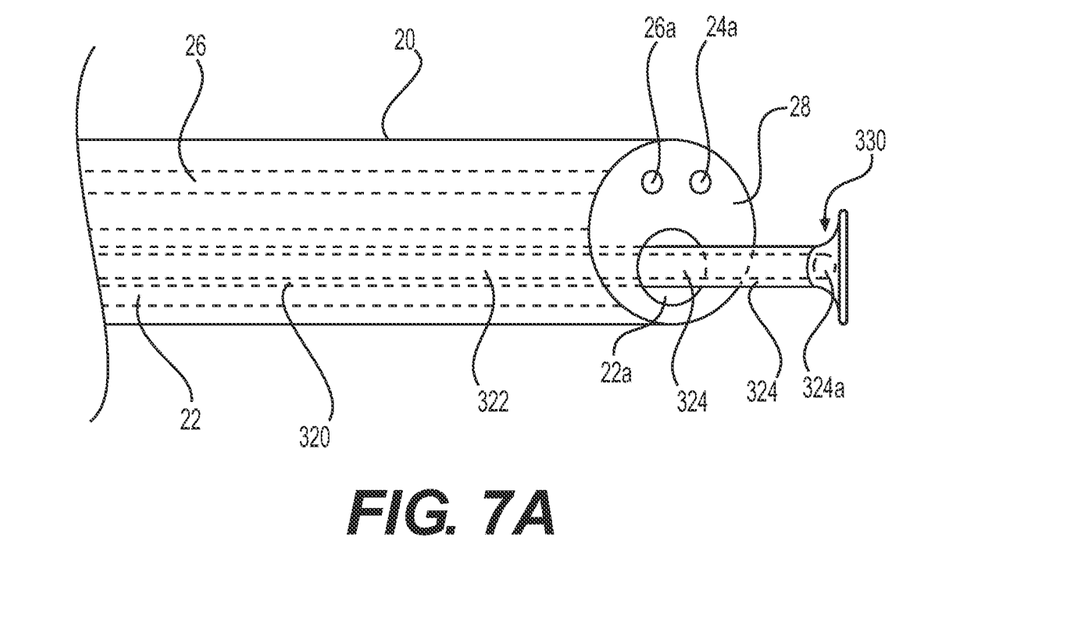
FIGS. 7A and 7B are perspective views of a medical tool of the medical system of FIG. 1, according to another embodiment.
Figure 7B:
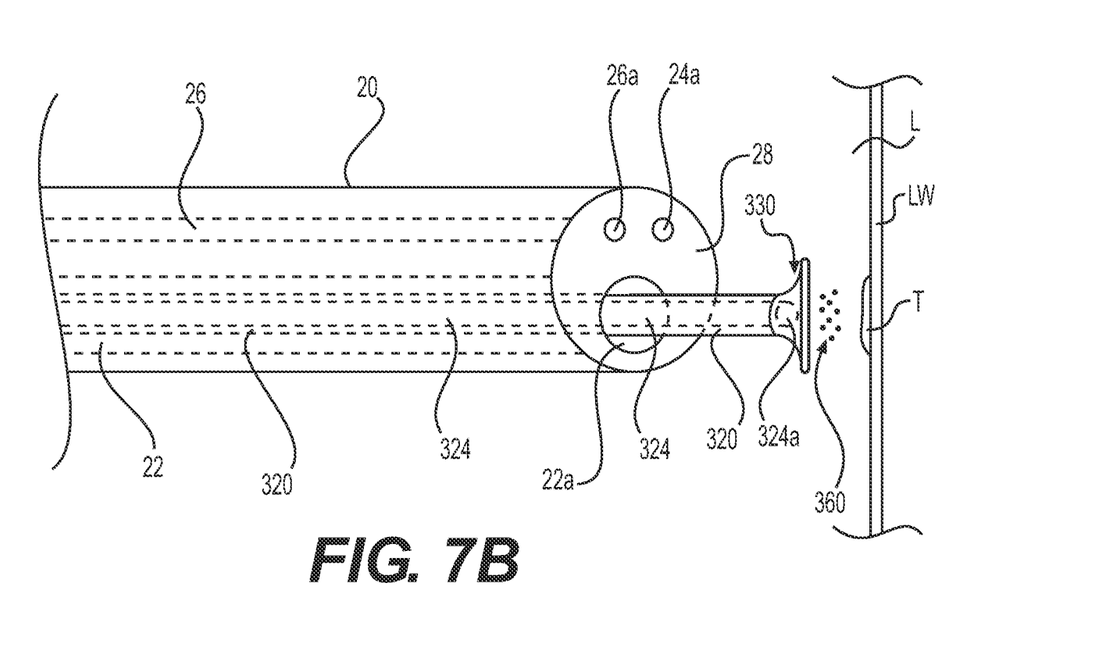
Figure 8A:
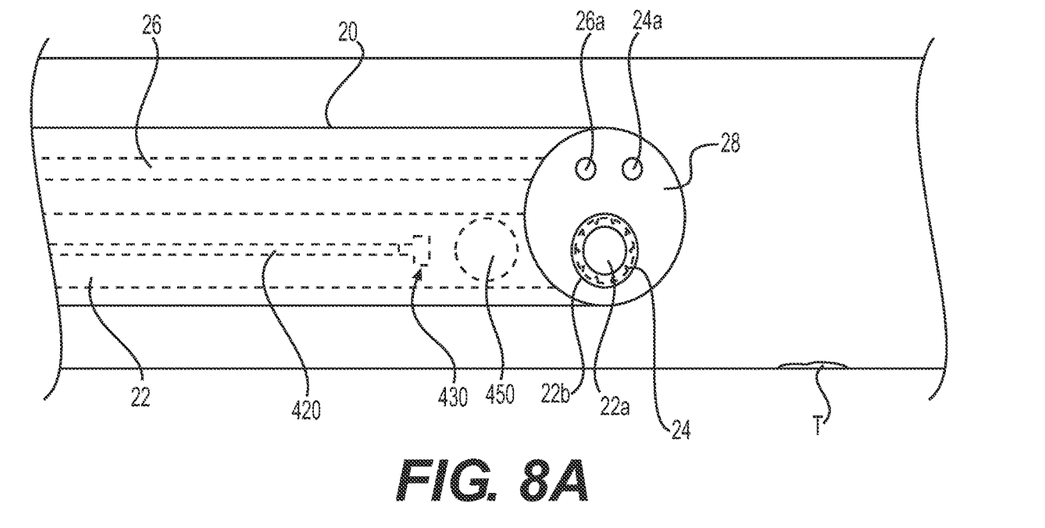
FIGS. 8A and 8B are perspective views of a medical tool of the medical system of FIG. 1, according to another embodiment.
Figure 8B:
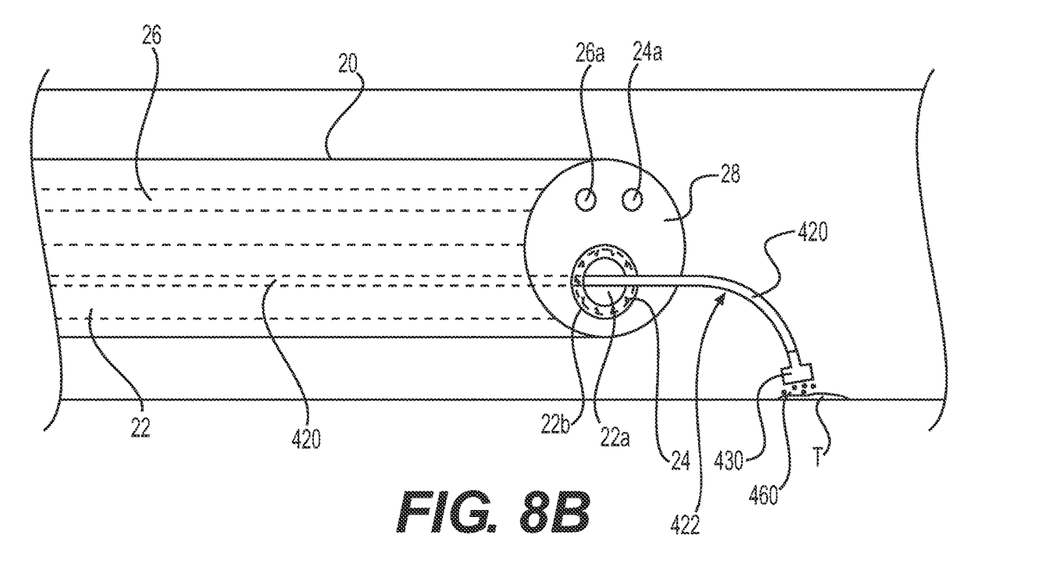

A distal end of medical system 10 according to another example is illustrated in FIGS. 6A-6C. Like elements are represented by like reference numerals.

As shown in FIG. 6A and similar to sheath 120 described above, sheath 220 extends through lumen 22 of catheter 20. Sheath 220 includes an end effector 230 at a distalmost end thereof. As shown in FIG. 6B, end effector 230 is umbrella shaped in a deployed position, such that a distalmost end of end effector 230 has a diameter greater than a proximalmost end of end effector 230. End effector 230 may be formed of a shape memory material, such as nitinol. When end effector 230 is exposed to lumen L, heat from the patient's body may increase the temperature of end effector 230, thereby causing the shape of end effector to change from a contracted shape to an umbrella shape. Alternatively, end effector 230 may include a collapsible structure that, when disposed within lumen 22, forms a collapsed or folded orientation, and when exposed from lumen 22, forms the umbrella shape shown in FIGS. 6B and 6C. Such a collapsible structure may be formed of a sheet of flexible material.

Referring to FIG. 6A, end effector 230 is collapsed when disposed within lumen 22. End effector 230 is configured to push a capsule 250, similar to capsule 140, out of first opening 22a in distal end face 28. An outer casing of capsule 250 begins to degrade once exposed to moisture, such as the mucosal membrane of lumen L or when sprayed with a fluid from openings 24a, 26a. FIG. 6B illustrates a release of a powder 260 from capsule 250 after the outer casing of capsule 250 has dissolved.

Referring to FIGS. 6B and 6C, end effector 230 captures or corals powder 260 on an inner, distal surface of the umbrella shaped end effector 230. According to an example, end effector 230 captures or corals capsule 250 before it is completely dissolved, allowing a greater amount of powder 260 to be captured by end effector 230 and is suspended in body lumen L. Alternatively, end effector 230 can capture powder 260 when powder 260 is not disposed in capsule 230.

As shown in FIG. 6C, sheath 220 may include an articulation section 222, similar to the articulation section described above, allowing a medical professional to manipulate end effector 230 to access target site T. End effector 230 may also be manipulated in any manner discussed above with respect to end effector 130, to bend toward target site T. For example, the medical professional maneuvers end effector 230 toward target site T such that the interior, distal surface of end effector 230 faces target site T, to direct powder 260 onto target site T. End effector 230 is urged against target site 260, placing pressure on powder 260 at target site T. To maximize the effect of powder 260 on target site T, a position of end effector 230 against target site T may be maintained for a predetermined amount of time. In this manner, the amount of powder 260 dispensed at target site T may be minimized while still maximizing the effectiveness of powder 260.

An operation of sheath 220 will now be described.

As discussed above, capsule 250 may be inserted through port 44, and a distal end of sheath 220 may be subsequently inserted through port 44, As with sheath 120, sheath 220 is pushed distally along lumen 22 using handle 140. End effector 230 pushes against a proximal end of capsule 250 to advance capsule 250 to a distal end of catheter 20, thereby causing end effector 230 and capsule 250 to exit first opening 22a.

When capsule 250 exits lumen 22, the medical professional may cause fluid to be emitted from opening 24a or opening 26a to cause an outer covering of capsule 250 to begin to dissolve or to fully dissolve. Alternatively, as discussed above, capsule 250 may dissolve based on the moisture already present in lumen L. At a same time or subsequently, as end effector 230 exits lumen 22 through opening 22a, end effector 230 expands from a collapsed shape to an expanded, umbrella shape, as shown in FIG. 6B, due to the physical properties of the material forming end effector 230 or via actuation of actuating cables or other actuation mechanism (not shown) to expand end effector 230.

Subsequently, sheath 220 is maneuvered to capture partially dissolved capsule 250 and/or powder 260. Sheath 220 is then maneuvered so that a distal surface of end effector 230 faces target site T via, e.g., articulation section 222, and the inner, distal surface of end effector 230 is urged toward target site T, allowing powder 260 to coat target site T. The distal surface of end effector 230 then may be placed in contact with target site T (and powder 260 coating target site T) and pressed against target site T. After a predetermined time period has elapsed, sheath 220 is moved proximally, causing end effector 230 to move into lumen 22 and collapse into the low-profile shape.

A distal end of medical system 10 according to another example is illustrated in FIGS. 7A and 7B. End effector 330 has a same umbrella shape as end effector 230 and may be formed of the same or similar materials and deployed in a same manner as end effector 230, as described above.

As shown in FIG. 7A, sheath 320 may be maneuvered in any manner described herein with reference to sheaths 120, 220 to access target site T, including but not limited to bending catheter 20 and/or bending sheath 330. Sheath 320 includes a central lumen 324, which extends from handle 40 to an interior of end effector 330 and terminates at a central opening 324*a*. As shown in FIG. 7B, end effector 330 extends from first opening 22*a* and faces and surrounds target site T. A capsule (not shown) containing a powder 360, or powder 360 without a capsule, is transmitted down central lumen 324 to target site T using any dispensing device known in the art. For example, a propellant fluid, such as $CO_2$ or the like, may force the capsule or powder 360 from a container attached at a proximal end of catheter 20, e.g., via handle 40, down central lumen 324, and out central opening 324*a*. An outer diameter of a distalmost end of end effector 330 defines the area in which the capsule or powder 360 is dispensed to target site T. For example, end effector 330 may be pressed against target site T to create a partial or complete seal between the interior, distal surface of end effector 330 and the wall of lumen L. In this manner, delivery of powder 360 may be targeted directly to target site T, while minimizing the amount of powder released outside of target site T.

An operation of sheath 320 will now be described.

Sheath 320 is pushed distally along lumen 22 using handle 140. End effector 330 exits first opening 22*a* and expands in a similar manner as end effector 230, e.g., based on the physical properties of the material forming end effector 330 or via actuation of actuating cables (not shown) to expand end effector 330.

After end effector 330 is exposed from first opening 22*a*, end effector 330 is maneuvered to cover target site T as shown in FIG. 7B. For example, an outer periphery of the distalmost end of end effector 330 is placed against a lumen wall LW of lumen L and/or against target site T. In some examples, the outer periphery of the distalmost end of end effector 330 completely surrounds target site T. In other embodiments, target site T may be larger and/or have a shape that is not capable of being completely surrounded by the outer periphery of the distalmost end of end effector 330. While target site T is shown as being generally parallel to distal end face 28, target site T may be angled, e.g., approximately perpendicular, to target site T. Accordingly, a distal end of sheath 320 may be articulated in a manner similar to the articulation of articulation section 222 disclosed herein, thereby accessing target site T.

Once end effector 330 is positioned against target site T, powder 360, e.g., a fluidized powder, a capsule, or some other delivery mechanism containing a therapeutic agent, is transmitted along central lumen 324 from a proximal end of sheath 320 to end effector 330. The powder is expelled from central lumen 324 via central opening 324*a*. Dispersal of powder 360 is limited to target site T surrounded by the outer periphery of end effector 330. Once powder 360 (transmitted via, e.g., fluidized powder, a capsule, or the like) contacts target T, powder 360 adheres via the moisture of the mucosal and/or a fluid which may be emitted via central lumen 324 and/or openings 24*a*, 26*a*. It will be understood that powder 360 may be transmitted along central lumen 324 by any actuation device, e.g., by actuation device 540 shown in FIG. 9 and discussed in greater detail herein, or any other known delivery mechanism.

Another example of a sheath 420 for deploying therapeutic material is shown in FIGS. 8A and 8B. As shown in FIG. 8A, sheath 420 includes an end effector 430 having a stamp- or press-like shape. The shape of end effector 430 may be cylindrical or disk-shaped. End effector 430 has a flat or substantially flat distalmost end with a circumference greater than a proximalmost end of end effector 430 and sheath 420, and the proximalmost end is connected to a distalmost end of sheath 420. It will be understood that the shape is not limited to a stamp- or press-like shape, and the shape of end effector 430 may include a shape that aids in capturing a capsule or a powder, as described herein.

Capsule 450 is positioned distally of end effector 430 in lumen 22. First opening 22*a* in FIG. 8A includes a ring 22*b* to narrow first opening 22*a* (relative to a cross-sectional size or diameter of lumen 22). In some embodiments, ring 22*b* includes teeth 24, or other sharp structures like hooks or barbs, located on a proximal side of ring 22*b* or extending radially inward from an inner perimeter of ring 22*b*. An outer diameter of capsule 450 is greater than a diameter of first opening 22*a*. As sheath 430 is moved distally with respect to catheter 20, end effector 430 pushes against a proximal side of capsule 450 and capsule 450 is urged against ring 22*b*. The force of urging capsule 450 against ring 22*b*, and in some embodiments teeth 24 or other sharp structure, causes capsule 450 to rupture, releasing powder 460. Opening 22a includes an inner diameter larger than the outer diameter of end effector 430 such that, as sheath 420 continues to be moved distally, end effector 430 is exposed from lumen 22 via opening 22a. Powder 460 coats the distalmost surface of end effector 430 and, as with other embodiments described herein, sheath 420 may be maneuvered toward target site T, such as by a bending section 422. Powder 460 may adhere to target site T either by the moisture of lumen L, or when exposed to a fluid emitted from openings 24a, 26a. A position of end effector 430 against target site T, and pressure applied to target site T by end effector 430, may be maintained for a predetermined period of time to ensure a suitable amount of powder adheres to treatment site T and is effective, for example, to stop a bleed. It will be understood that ring 22b and teeth 24 may be used in any sheath described herein to assist in rupturing a capsule to expose and deliver a material or a powder disposed in the capsule. In addition, in some embodiments, no sharp structure is present on ring 22b, and forcing capsule 450 through the smaller diameter opening 22a will rupture capsule 450 to disperse powder 460.

An operation of sheath 420 will now be described.

As with the other sheaths described herein, capsule 450 is inserted through port 44 prior to inserting a distal end of sheath 420 into port 44. Sheath 420 is pushed distally along lumen 22 using handle 140, which causes end effector 430 to push against the proximal end of capsule 450, causing end effector 430 and capsule 450 to approach first opening 22a. As capsule 450 and end effector 430 approach first opening 22a, a distal end of capsule 450 contacts a surface of ring 22b facing an interior of lumen 22 and/or teeth 24 or other sharp structure arranged on an inner face or inner circumference of ring 22b. A force of end effector 430 against the proximal end of capsule 450 and a force of ring 22b and/or teeth 24 against the distal end of capsule 450 causes capsule 450 to rupture, expelling powder 460.

A user continues to push sheath 420 distally, causing powder 460 to contact a distalmost end of end effector 430. Sheath 420 is then maneuvered to face target site T in any manner described herein, e.g., via articulation of articulation section 422, urging end effector 430 toward target site T. End effector 430 tamps or pushes powder 460 against target tissue T. Powder 460 may be activated by moisture, e.g., a mucosal fluid at target site T and/or fluid sprayed via openings 24a, 26a. After a predetermined time period has elapsed, sheath 420 is moved proximally, causing end effector 430 move back into lumen 22.

Figure 9:
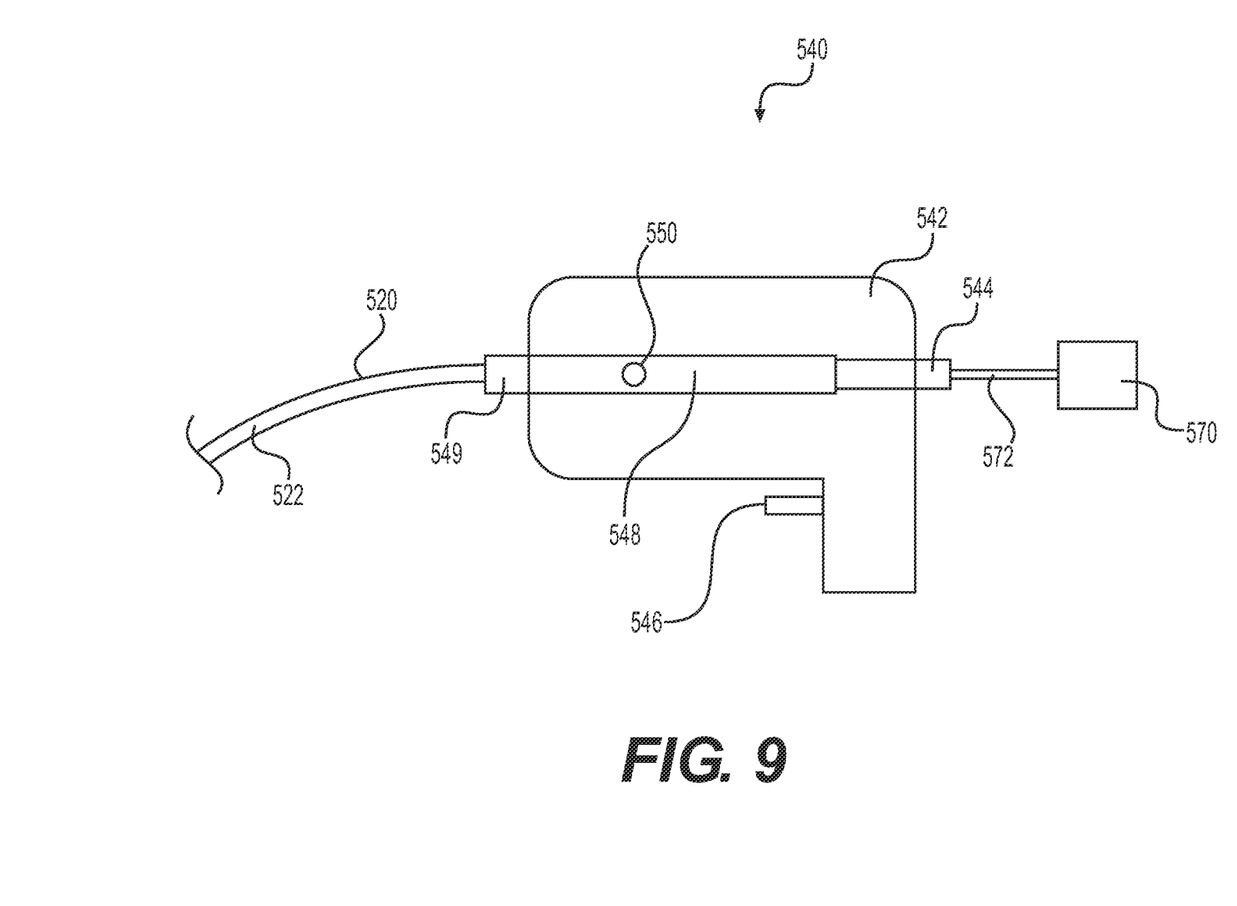
FIG. 9 is a perspective view of an actuation device, according to an embodiment.

An actuation device 540 for dispensing powder and/or a capsule 550 is shown in FIG. 9. Actuation device 540 includes a body 542 having a pistol-shaped grip and a trigger mechanism 546. A fluid connector 544 connects actuation device 540 to a pressurized fluid source 570, e.g., $CO_2$, via a hose 572 (e.g., a flexible hose). Fluid source 570 may be a pressurized fluid source in a hospital, or fluid source 570 may be a device attached directly to actuation device 540, allowing actuation device 540 to be portable.

Fluid connector 544 is connected to internal chamber 548, which may contain capsule 550 or a powder not contained within a capsule. Capsule 550 may be added individually, or a hopper or other container (not shown) may be attached to actuation device 540 to supply capsules or powder to internal chamber 548. A catheter connector 549 may connect a catheter 520, having a lumen 522, to body 542. Once trigger mechanism 546 is actuated, a propellant fluid, e.g., $CO_2$, is released from pressurized fluid source 570, and may transmit capsule 550 distally down lumen 522 to an outlet (not shown) at a distal end of catheter 520. According to an example, an amount of gas released may be approximately 16 liters or less, e.g., equal to an amount of gas, such as $CO_2$, stored in two standard cartridges, at a pressure of approximately 1 to 10 Standard Liters per Minute (SLPM), or approximately 5 SLPM. This amount of propellant gas is sufficient to transmit capsule 550 along lumen 522, while also being a safe amount of propellant fluid to supply to a body that is insufflated.

An operation of actuation device 540 will now be described.

Capsule 550 is loaded into internal chamber 548. Catheter 520 is introduced to a body via a natural orifice or an incision and advanced to a target site. Once the distal end of catheter 520 is positioned adjacent the target site, the user actuates trigger mechanism 546, causing propellant fluid to exit fluid source 570 and enter internal chamber 548. The propellant fluid causes capsule 550 to travel distally from internal chamber 548 to the target tissue via catheter 520. The propellant fluid is sufficient to transmit capsule 550 along catheter 520, while being a safe amount of propellant fluid to introduce to a body that is insufflated. Additional capsules 550 may be transmitted to the same or different target sites until the treatment is complete, at which point catheter 520 is removed from the body.

It will be apparent to those skilled in the art that various modifications and variations can be made to the disclosed device without departing from the scope of the disclosure. For example, any material or fluid may be contained in the capsules and/or transmitted in powder form to be expelled from the application device to a target location, including but not limited to materials having therapeutic effects. Additionally, or alternatively, unless otherwise specified, the medical device described herein may be formed of any metal, alloy, plastic, or ceramic, or any combination thereof, suitable for use in medical applications. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:
   a handle;
   a sheath extending from a distal end of the handle;
   a catheter including a catheter lumen, wherein the sheath is configured to extend through the catheter lumen;
   a capsule containing a material, wherein the capsule includes a tether, the tether is woven through a wall of the capsule; and
   an end effector connected to a distal end of the sheath and configured to grasp the tether,
   wherein the end effector is configured to advance the capsule along the catheter lumen and to a target site via a catheter lumen opening at a distal end of the catheter, wherein an outer portion of the capsule includes a material configured to adhere to the target site when exposed to a fluid, and wherein the end effector is configured to cause release of the material from the capsule and onto the target site by applying a force on the tether once the capsule is adhered to the target site;
   wherein the capsule includes a first side and a second side configured to separate from the first side; and
   wherein the tether and the capsule are configured so that applying force to the tether separates the first side from the second side.

2. The medical system according to claim 1, wherein the distal end of the catheter or the sheath is configured to bend when the distal end of the sheath is distal of a distalmost end of the catheter.

3. The medical system of claim 1, wherein the material is a hemostatic powder or a therapeutic powder.

\* \* \* \* \*